US00PP25263P3

(12) United States Plant Patent
Pavlich

(10) Patent No.: US PP25,263 P3
(45) Date of Patent: Jan. 27, 2015

(54) *BEGONIA* PLANT NAMED 'COOL BREEZE EM'

(50) Latin Name: ***Begonia* hybrid**
Varietal Denomination: Cool Breeze Em

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 108 days.

(21) Appl. No.: 13/986,638

(22) Filed: May 20, 2013

(65) Prior Publication Data

US 2014/0345016 P1 Nov. 20, 2014

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Kent L Bell
(74) *Attorney, Agent, or Firm* — Klarquist Sparkman, LLP

(57) ABSTRACT

A new and distinct form of *Begonia* plant characterized by deep forest green leaves with a satiny sheen, leaves with dark red backs, dark red stems and petioles, a shrubby habit, and clusters of cherry pink flowers above the foliage in winter to early spring.

1 Drawing Sheet

Botanical denomination: *Begonia* hybrid.
Variety designation: 'Cool Breeze Em'.
Parentage: *Begonia hemsleyana*×*Begonia fangii*.

BACKGROUND OF THE INVENTION

The present invention relates to a new and distinct cultivar of *Begonia*, of the family Begoniaceae, and given the cultivar name, 'Cool Breeze Em'. This plant originated from planned breeding program for a colorful series of landscape *Begonia*. The new cultivar originated from a cross between an unnamed plant of *Begonia hemsleyana*, as the seed parent, and an unnamed plant of *Begonia fangii*, as the pollen parent. This selection is uniquely characterized by:

1. broad leaves of deep forest green with a satiny sheen,
2. leaves with dark red backs, dark red stems and petioles,
3. a bushy habit, and
4. clusters of cherry pink flowers above the foliage in winter to early spring.

Compared to the seed parent an unnamed plant of *Begonia hemsleyana*, the new cultivar has leaves shallowly palmately lobed rather than palmately compound. Compared to the pollen parent, an unnamed plant of *Begonia fangii*, the new cultivar is broader in habit, better branched, and with leaves that are shallowly palmately lobed rather than palmately compound.

This *Begonia* is unique. There are no similar ones on the market known to the breeder.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers of *Begonia* 'Cool Breeze Em'.

FIG. 2 shows two 1-and-a-half year old plants in a growing side by side in the garden in August in Canby, Oreg.

DETAILED PLANT DESCRIPTION

The following is a detailed description of the new *Begonia* cultivar based on observations of a one-year-old specimen grown in a one gallon container outside in shade in early November in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The *Royal Horticultural Society Colour Chart*, $5^{th}$ edition.

Plant:
- *Type.*—Herbaceous rhizomatous perennial.
- *Form.*—Clumping, caulescent.
- *Cold hardiness.*—USDA Zone 10.
- *Size.*—Grows to 33 cm tall and 50 cm wide.
- *Vigor.*—Excellent.

Stem:
- *Type.*—Upright.
- *Size.*—Grows to 16 cm long and 11 mm wide.
- *Internodes.*—From 2 cm to 8 cm long.
- *Surface.*—Pubescent.
- *Color.*—Greyed Purple 187A.

Leaf:
- *Type.*—Simple.
- *Arrangement.*—Basal and alternate.
- *Shape.*—Reniform overall.

*Lobing/division.*—Irregularly shallowly palmately 3 to 7 lobed.

*Venation.*—Palmate, Greyed Purple 187B on topside, 187A on bottom side.

*Margins.*—Toothed.

*Apex.*—Acute.

*Base.*—Cordate, oblique.

*Blade size.*—Grows to 19 cm wide and 17 cm long.

*Surface texture.*—Pubescent on top and bottom.

*Stipules.*—Deciduous, ovate-lanceolate, 20 mm long and 13 mm wide, apex acuminate and cuspidate, entire, back side pubescent, inside glabrous, both sides Greyed Red 182A.

*Petiole description.*—Grows to 27 cm long and 9 mm wide, succulent, pubescent, Grayed Purple 187A.

*Leaf color.*—Top side between Greyed Green N189A and Black 202A; bottom side Greyed Purple 187A.

Inflorescence:

*Type.*—Axillary, bisexual, cymose.

*Number of flowers per cyme.*—4 to 6.

*Peduncle description.*—Grows 8.5 cm long and 4 mm wide, glabrous, fleshy, Greyed Purple 187A; with 2 opposite, dehiscent petiolate leaf-bracts below each cyme, which grow to 12 mm wide and 19 mm long, margins entire on the bottom half and irregularly incised on the top half, back side pubescent, inside glabrous, both sides Greyed Red 182A.

*Pedicel description.*—Grow to 15 mm long, 1.5 mm wide, fleshy, glabrous, Greyed Purple 187C.

*Bloom period.*—Late fall to early winter in Canby, Oreg.

Flower bud:

*Size.*—Staminate flower bud 15 mm long and 11 mm wide prior to opening; pistillate flower bud 20 mm deep and 18 mm wide prior to opening.

*Color.*—Red Purple 60D on tepal area, Red Purple 60A on ovary.

Flower:

*Type.*—Monoecious, bilaterally symmetrical.

*Pistillate flower.*—Grows to 20 mm deep and 32 mm wide overall; 4 fleshy tepals, 16 mm long and 13 mm wide, broadly elliptical, cupped, tip and base obtuse, margins entire, glabrous and Red Purple 62B on both sides, Red Purple N57C up the middle on back side; ovary to 18 mm wide and 11 mm deep, three winged, two equal and one longer, Red Purple 60A, style 2 branched, stigma 2 branched and twisted, style 5 mm long and Greyed Red 182D, stigma 3 mm deep and 7 mm wide overall, Green Yellow 1D.

*Staminate flower.*—11 mm deep and 25 mm wide, 4 overlapping tepals, 2 larger outer tepals 15 mm long and 8 mm wide, cupped, broadly elliptical, margin entire, tip obtuse, base cuneate, Red 51A inside and Red 47A outside; inner tepals grow to 10 mm long and 8 mm wide, broadly elliptical, entire, tip obtuse, base attenuate, both sides Red 54C; stamen many in a globular head 8 mm in diameter, stalk 2 mm long and Greyed Yellow 161C, filaments 1.5 mm long and Yellow 8D, anthers 1.5 mm long and Red Purple 65D, anthers and pollen Yellow Orange 20A.

*Fragrance.*—None.

*Lastingness.*—A cyme blooms for about 4 weeks on the plant.

Fruit and seed: None seen.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

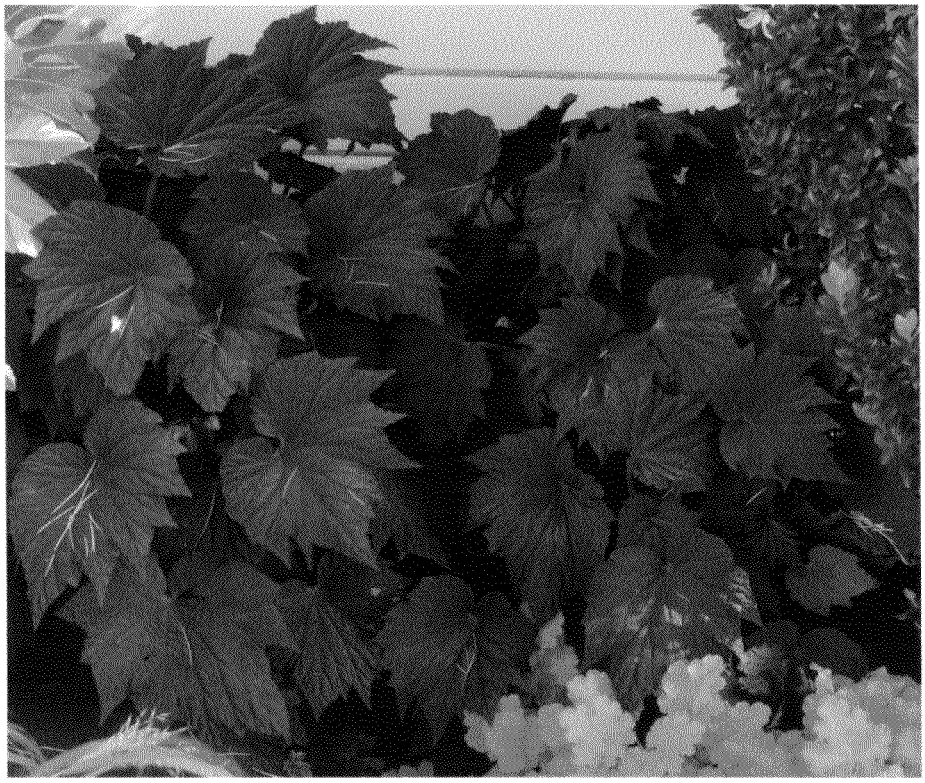

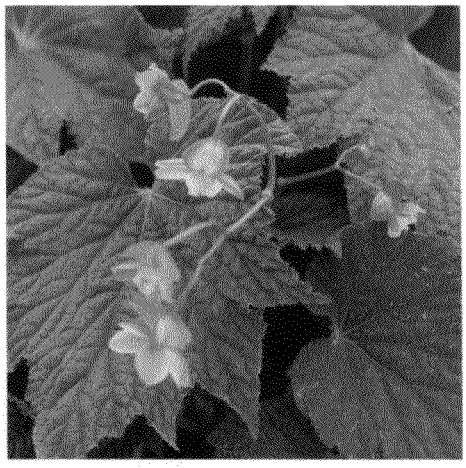
FIG. 1 on right,
FIG. 2 below